United States Patent
Oshry et al.

(10) Patent No.: US 9,814,675 B2
(45) Date of Patent: Nov. 14, 2017

(54) AQUEOUS GEL COMPOSITION AND METHODS OF USE

(71) Applicant: Elle Pharmaceutical, LLC, Weston, MA (US)

(72) Inventors: Lauren Oshry, Weston, MA (US); Elias Reichel, Weston, MA (US)

(73) Assignee: ELLE PHARMACEUTICAL, LLC, Weston, MA (US)

( * ) Notice: Subject to any disclaimer, the term of this patent is extended or adjusted under 35 U.S.C. 154(b) by 0 days.

(21) Appl. No.: 15/411,252

(22) Filed: Jan. 20, 2017

(65) Prior Publication Data

US 2017/0239180 A1 Aug. 24, 2017

Related U.S. Application Data

(60) Provisional application No. 62/298,524, filed on Feb. 23, 2016.

(51) Int. Cl.

| A61K 31/16 | (2006.01) |
|---|---|
| A61K 31/165 | (2006.01) |
| A61K 31/47 | (2006.01) |
| A61K 9/06 | (2006.01) |
| A61K 9/00 | (2006.01) |
| A61K 31/167 | (2006.01) |
| A61K 47/38 | (2006.01) |
| A61K 47/14 | (2017.01) |

(52) U.S. Cl.
CPC .............. *A61K 9/06* (2013.01); *A61K 9/0014* (2013.01); *A61K 9/0034* (2013.01); *A61K 31/167* (2013.01); *A61K 47/14* (2013.01); *A61K 47/38* (2013.01)

(58) Field of Classification Search
CPC .... A61K 31/445; A61K 31/165; A61K 31/16; C07D 401/04
USPC ................................ 514/312, 330, 619, 626
See application file for complete search history.

(56) References Cited

U.S. PATENT DOCUMENTS

| 7,005,408 B2 * | 2/2006 | Ahmad | A61K 9/0034 424/DIG. 14 |
| 2009/0185995 A1 * | 7/2009 | Vochecowicz | A61K 9/0034 424/78.02 |
| 2017/0239181 A1 * | 8/2017 | Oshry | A61K 9/06 |

* cited by examiner

*Primary Examiner* — Raymond J Henley, III
(74) *Attorney, Agent, or Firm* — Wood, Phillips, Katz, Clark & Mortimer

(57) ABSTRACT

The present invention is directed to an aqueous gel composition containing a local anesthetic, a lubricating agent, and a preservative and methods of treating vaginal pain, such as dyspareunia by topically administering said composition.

20 Claims, No Drawings

AQUEOUS GEL COMPOSITION AND METHODS OF USE

BACKGROUND OF THE INVENTION

Dyspareunia is the medical term for painful sexual intercourse. Dyspareunia is defined as persistent or recurrent genital pain that occurs just before, during or after intercourse. It is estimated that as many as 60% of women experience painful intercourse at some point in their lives. Heim L J, Evaluation and differential diagnosis of dyspareunia, Am Fam Physician, 2001 Apr. 15, 63(8), 1535-1544. Painful intercourse can occur for a variety of reasons—ranging from structural problems to psychological concerns. Elements of the history and physical examination help to identify the etiology and guide treatment, in most cases. Perivaginal infections, for example, may be treated with antibiotic or antifungal mediations based on microscopy or culture results. Endometriosis may be treated with non-steroidal anti-inflammatory drugs, contraceptives or gonadotropin-releasing hormone agonists. Uterine myomas may be treated with surgery. Seehusen D A, et al., Dyspareunia in Women, Am Fam Physician, 2014 Oct. 1, 90(7), 465-470.

Genitourinary symptoms are common in postmenopausal women, including vaginal dryness and dyspareunia—which are "the most bothersome symptoms" in clinical trials. Ettinger B, et al., Measuring symptom relief in studies of vaginal and vulvar atrophy: the most bothersome symptom approach. Menopause, 2008 September-October, 15(5), 885-889. It is estimated that 84.2% of woman at 6 years post menopause will manifest genitourinary syndrome of menopause ("GSM"), with 100% of those reporting vaginal dryness and 77.6% reporting dyspareunia. Palma F, et al., Vaginal atrophy of women in postmenopause. Results from a multicentric observational study: The AGATA study. Maturitas, 2016 January, 83, 40-44. Traditionally this had been felt to be related to decline in estrogen with atrophy of vulvar, vaginal and urinary tract epithelium, tissues which are rich in estrogen receptors; and a decline in lubrication as well as increase in vaginal pH, and was referred to as vulvovaginal atrophy or atrophic vaginitis. In 2014, the International Society for the Study of Women's Sexual Health (ISSWSH) and the North American Menopause Society (NAMS) agreed that the term genitourinary syndrome of menopause (GSM) was a more accurate and acceptable term. GSM encompasses both symptoms including,: genital dryness, decreased lubrication with sexual activity, discomfort or pain with sexual activity, post-coital bleeding, decreased arousal, irritation/burning/itching of vulva or vagina, dysuria, and urinary frequency/urgency as well as the following signs including, decreased moisture, decreased elasticity, resorption of labia minora, pallor/erythema, loss of vaginal rugae, tissue fragility, urethral eversion or prolapse, introital retraction and recurrent urinary tract infections. Supportive findings include a pH greater than 5, increased parabasal cell on maturation index and decreased superficial cells. The presumptive etiology of this syndrome is related to a decline in estrogen, leading to atrophic changes in the vulvovaginal tissues, decrease in lubrication, and an increase in pH. Portman, D J, et al., Genitourinary syndrome of menopause: new terminology for vulvovaginal atrophy from the International Society for the Study of Women's Sexual Health and The North American Menopause Society, J Sex Med, 2014 December, 11(12), 2865-72. Treatments have focused on increasing the thickness of the tissues and/or lowering the vaginal pH. Treatments effective in achieving these objectives have included estrogens (topically or systemically) or the selective estrogen receptor modulator, ospemifene. Sturdee D W, et al., Recommendations for the management of postmenopausal vaginal atrophy, Climacteric 2010 December, 13(6), 509-522; Bachmann G A, et al., Ospemifene Study Group. Ospemifene effectively treats vulvovaginal atrophy in post-menopausal women: results from a pivotal phase 3 study, Menopause, 2010 May-June, 17(3), 480-486. Non-hormonal therapies include vaginal lubricants and moisturizers, which do not reverse atrophic changes but enhance comfort.

A review of several large studies examining the relationship between vaginal atrophy and dyspareunia, however, found no association between the occurrence or severity of atrophy of vaginal tissues and post-menopausal dyspareunia. Kao A, et al., Dyspareunia in postmenopausal women: A critical review. Pain Res Manag, 2008 May-June, 13(3), 243-254. Recent studies suggest that another mechanism, related to hyperproliferation of a neural network in the vulvar vestibule,—part of the external female genitalia anterior to the vagina, which is commonly seen in estrogen deficient states and may be an important mediator of dyspareunia in the genitourinary syndrome of menopause. Leclair, C M, et al. Histopathologic characteristics of menopausal vestibulodynia Obstet Gynecol, 2013 October, 122 (4), 787-793; Goetsch, M F, et al., Locating pain in breast cancer survivors experiencing dyspareunia: a randomized controlled trial Obstet Gynecol, 2014 June, 123(6), 1231-1236. The application of topical anesthetic (4% lidocaine aqueous solution) to the localized area of pain in the vulvar vestibule, in conjunction with silicone based lubricant, has been shown to effectively extinguish this pain, without side effects, and to enable comfortable intercourse in breast cancer survivors with dyspareunia. Goetsch M F, et al., A practical solution for dyspareunia in breast cancer survivors: a randomized controlled trial, J Clin Oncol, 2015 Oct. 20, 33(30), 3394-3400.

Prior art attempts at creating an effective aqueous gel for vaginal use include United States Patent Application No. 2016/0220601 ("the 601 application") directed to a composition for vaginal application containing a sulfated polysaccharide, a natural quaternary polymer, a quaternary molecular compound, a metalloproteinase inhibitor anti-inflammatory agent and an acid pH buffering system. This specific combination is shown to be necessary to provide optimal lubrication and hydration as the composition is directed to reducing irritation and strengthening vaginal tissue among others conditions.

Prior art attempts at creating a local anesthetic gel include WIPO Publication No. 2015/177288 ("the '288 application") directed to an aqueous gel formulation suitable for oral use containing an anesthetic, a polyethylene oxide, a polysaccharide and a preservative. However, the '288 publication requires a polyethylene oxide to obtain its desired properties such as being stringent without being tacky. U.S. Pat. No. 8,759,401 ("the '401 patent"), assigned to Akorn, Inc., is directed to an aqueous gel formulation suitable for administration to the eye containing lidocaine hydrochloride, a viscoelastic polymer and sodium chloride. However, the '401 patent requires a pH of at least 5.0 and no preservatives because of the need to be comfortably applied to the eye.

Thus, there remains a need in the art for aqueous gel formulations that are specifically formulated to topically treat vulvovaginal pain.

SUMMARY OF THE INVENTION

The present invention is directed to topical aqueous gel compositions for treating vulvovaginal pain. This aqueous gel composition is particularly useful for alleviating vulvovaginal pain that occurs during sexual activity, such as dyspareunia. Compositions of the present invention are specifically formulated with a particular pH and optional osmolality range that was discovered to be both comfortable and effective when applied to the vulvovaginal region and to create a stable composition for a topical anesthetic. Further, compositions of the present invention have a viscosity range that allows it be both comfortable and effective for use during sexual activity.

In one embodiment, the present invention is directed to an aqueous gel composition comprising, consisting essentially of or consisting of:

an effective amount of a local anesthetic, preferably selected from the group consisting of lidocaine, procaine, ropivacaine, bupivacaine, prilocaine, dibucaine and salts thereof, more preferably lidocaine or salts thereof;

a lubricating agent, preferably a viscoelastic polymer, more preferably a cellulose derivative, even more preferably hydroxypropylmethyl cellulose ("HPMC");

a preservative, selected from the group consisting of methyl paraben, propyl paraben, butyl paraben, benzyl paraben, methylcellulose, polyethylene glycol, polyvinylpyrrolidone, polyoxyethylene monostearate, polyoxyethylene sorbitan monolaurate, polyoxyethylene sorbitan monooleate and a combination thereof, more preferably methyl paraben; and optionally, an osmolality modifier, preferably selected from the group consisting of sodium chloride, potassium chloride, calcium chloride, dextrose, glycerin, propylene glycol, mannitol, sorbitol, xylitol, trehalose, and sucrose, more preferably sodium chloride;

wherein the composition has a pH from about 3.5 to about 4.5 and a viscosity from about 2,000 to about 8,000 centipoise ("cps") and is topically administered to the vulvovaginal region, preferably the vulvar vestibule.

In another embodiment, the composition of the present invention is free of polyethylene oxides and sulfated polysaccharides.

In a preferred embodiment, the present invention is directed to an aqueous gel composition comprising, consisting essentially of or consisting of from about 3.5% to about 4.0% w/v of a local anesthetic, preferably lidocaine or salts thereof, from about 2% to about 3% w/v of a lubricating agent, preferably HPMC, from about 0.07% to about 0.09% w/v of a preservative, preferably methyl paraben, and optionally, an osmolality modifier, preferably sodium chloride, at a concentration that provides the composition an osmolality from about 270 to about 310 milliosmoles per liter ("mOsm/L"), wherein the composition has a pH from about 3.5 to about 4.5 and a viscosity from about 2,000 to about 8,000 cps and is topically administered to the vulvovaginal region, preferably the vulvar vestibule.

In another preferred embodiment, the present invention is directed to an aqueous gel composition comprising, consisting essentially of or consisting of about 3.75% w/v lidocaine or salts thereof, preferably lidocaine hydrochloride, 2.25% w/v hydroxypropylmethyl cellulose, 0.07% w/v methyl paraben, and optionally, sodium chloride at a concentration that provides an osmolality of about 290 mOsm/L, wherein the composition has a pH of about 4.5 and the viscosity of the composition is of about 6,100 cps and is topically administered to the vulvar vestibule.

The present invention is further directed to a method of treating vulvovaginal pain, including dyspareunia, including dyspareunia associated with genitourinary syndrome of menopause, comprising topically administering the composition of the present invention to a patient in need thereof, preferably administration occurs immediately prior to sexual activity.

DETAILED DESCRIPTION OF THE INVENTION

The vulvovaginal region provides a challenging environment that presents unique obstacles in formulating comfortable and effective topical medications. In particular, the vulvovaginal region requires a particular pH that differs from other mucosal surfaces such as those found in the mouth, eyes and epidermis. Further, many topical medications for vulvovaginal use must also be capable of withstanding shear forces not encountered at other mucosal surfaces, such as those caused by sexual activity. The aqueous gel composition of the present invention was discovered to be chemically stable and to be comfortable and effective upon topical application to the vulvovaginal region and to maintain these properties during sexual activity.

In one embodiment, the present invention is directed to an aqueous gel composition comprising, consisting essentially of or consisting of:

a local anesthetic, preferably, selected from the group consisting of lidocaine, procaine, ropivacaine, bupivacaine, prilocaine and dibucaine and salts thereof, preferably lidocaine or salts thereof;

a lubricating agent, preferably a viscoelastic polymer, more preferably a cellulose derivative, even more preferably hydroxypropylmethyl cellulose ("HPMC"), a preservative, selected from the group consisting of methyl paraben, propyl paraben, butyl paraben, benzyl paraben, methylcellulose, polyethylene glycol, polyvinylpyrrolidone, polyoxyethylene monostearate, polyoxyethylene sorbitan monolaurate, polyoxyethylene sorbitan monooleate and a combination thereof, more preferably methyl paraben; and an osmolality modifier, preferably selected from the group consisting of sodium chloride, potassium chloride, calcium chloride, dextrose, glycerin, propylene glycol, mannitol, sorbitol, xylitol, trehalose, sucrose and a combination thereof, preferably sodium chloride, wherein the composition has a pH from about 3.5 to about 4.5 and a viscosity from about 2,000 to about 8,000 centipoise ("cps") and is topically administered to the vulvovaginal region, preferably the vulvar vestibule.

In another embodiment, the composition of the present invention is free of polyethylene oxides and sulfated polysaccharides.

In a preferred embodiment, the present invention is directed to an aqueous gel composition comprising, consisting essentially of or consisting of from about 3.5% to about 4.0% w/v of a local anesthetic, preferably lidocaine or salts thereof, from about 2% to about 3% w/v of a lubricating agent, preferably HPMC, from about 0.07% to about 0.09% w/v of a preservative, preferably methyl paraben and optionally, an osmolality modifier at a concentration that provides the composition an osmolality from about 270 to about 310 mOsm/L, preferably from about 280 to about 300 mOsm/L, more preferably about 290 mOsm/L, wherein the composition has a pH from about 3.5 to about 4.5 and a viscosity from about 2,000 to about 8,000 cps and is topically administered to the vulvovaginal region, preferably the vulvar vestibule.

In another preferred embodiment, the present invention is directed to an aqueous gel composition comprising, consisting essentially of or consisting of about 3.75% w/v lidocaine or salts thereof, preferably lidocaine hydrochloride, about 2.25% w/v hydroxypropylmethyl cellulose, about 0.07% w/v methyl paraben, and optionally, sodium chloride at a concentration that provides an osmolality of about 290 mOsm/L, wherein the composition has a pH of about 4.5 and the viscosity of the composition is of about 6,100 cps and is topically administered to the vulvar vestibule.

The present invention is further directed to a method of treating vulvovaginal pain, including dyspareunia, including dyspareunia is associated with genitourinary syndrome of menopause, comprising topically administering compositions of the present invention to a patient in need thereof, preferably administration occurs immediately prior to sexual activity.

Definitions

As used herein the terms "treat," "treating" or "treatment" refer to preventing or alleviating pain.

As used herein the term "patient" refers but is not limited to a person that is being treated for vaginal pain or another affliction or disease that can be treated with a topical anesthetic.

As used herein "vulvovaginal pain" refers to pain localized in the female reproductive tract, e.g., the vulva including the vulvar vestibule, vagina, cervix and combinations thereof. The pain can be due to a medical condition, psychological condition and/or sexual activity.

As used herein the term "vulvovaginal" or "vulvovaginal region" refers to the vulva including the vulvar vestibule, the vagina, the cervix and combinations thereof.

As used herein "sexual activity" refers to any activity involving penetration of the vagina. Examples of sexual activity are masturbation, sexual intercourse, and the like.

As used herein "dyspareunia" refers to pain during sexual intercourse.

As used herein "genitourinary syndrome of menopause" refers to a collection of symptoms and signs associated with a decrease in estrogen and other sex steroids involving changes to the labia majora/minora, clitoris, vestibule/introitus, vagina, urethra and bladder. The syndrome may include but is not limited to genital symptoms of dryness, burning, and irritation; sexual symptoms of lack of lubrication, discomfort or pain, and impaired function; and urinary symptoms of urgency, dysuria and recurrent urinary tract infections.

As used herein the term "effective amount" refers to the amount necessary to treat a patient in need thereof.

As used herein "immediately prior" refers to no more than 5 minutes prior to the of the onset of sexual activity involving the vulvovaginal region.

As used herein "w/v" refers to weight by volume of the total composition.

As used herein, all numerical values relating to amounts, weights, and the like, that are defined as "about" each particular value is plus or minus 10%. For example, the phrase "about 10% w/v" is to be understood as "9% to 11% w/v". Therefore, amounts within 10% of the claimed value are encompassed by the scope of the claims.

Local anesthetics suitable for use in the present invention include, but are not limited to, lidocaine, procaine, ropivacaine, bupivacaine, prilocaine and dibucaine and salts thereof, preferably lidocaine or salts thereof, more preferably lidocaine hydrochloride.

As used herein "salts" refers to those salts which retain the biological effectiveness and properties of the parent compounds and which are not biologically or otherwise harmful at the dosage administered. Salts of the compounds of the present inventions may be prepared from inorganic or organic acids or bases.

Salts of active agents of the present invention include, but are not limited to, acid addition salts. For example, the nitrogen atoms may form salts with acids. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form acid addition salts include such inorganic acids as hydrochloric acid, hydrobromic acid, sulfuric acid and phosphoric acid and such organic acids as oxalic acid, maleic acid, succinic acid and citric acid.

Salts of active agents of the present invention also include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethyl ammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

Lubricating agents suitable for use in the present invention include, but are not limited to, viscoelastic polymers such as a polysaccharide, in particular cellulose and its derivatives such as a cellulose ether with methyl and/or ethyl and/or propyl groups, in particular hydroxypropyl methylcellulose, hydroxyethyl methylcellulose and/or methylcellulose, a glycosaminoglycan, in particular hyaluronic acid, chondroitin sulphate, dermatan sulphate, heparin, heparan sulphate, keratan sulphate, alginic acid, polymannuronic acid, polyguluronic acid, polyglucuronic acid, amylose, amylopectin, callose, chitosan, polygalactomannan, dextran, xanthan and/or a mixture thereof, preferably a cellulose derivative, preferably hydroxypropylmethyl cellulose.

Osmolality modifiers suitable for use in the present invention include, but are not limited to ionic salts, such as sodium chloride, potassium chloride, and calcium chloride, nonionic agents, such as dextrose, glycerin, propylene glycol, mannitol, sorbitol, xylitol, trehalose, and sucrose, more preferably sodium chloride, at a concentration that provides the composition an osmolality from about 270 to about 310 mOsm/L, preferably from about 280 to about 300 mOsm/L, and more preferably, about 290 mOsm/L.

Preservatives suitable for use in the present invention include, but are not limited to, methyl paraben, propyl paraben, butyl paraben, benzyl paraben, methylcellulose, polyethylene glycol, polyvinylpyrrolidone, polyoxyethylene monostearate, polyoxyethylene sorbitan monolaurate, polyoxyethylene sorbitan monooleate and a combination thereof, preferably methyl paraben or a combination of methyl paraben and propyl paraben. Preservatives may be at a concentration from about 0.01% to about 1% w/v, preferably from about 0.07% to about 0.09% w/v and more preferably at 0.02% w/v, 0.07% w/v and 0.09% w/v.

Throughout the application, the singular forms "a," "an," and "the" include plural reference unless the context clearly dictates otherwise.

The disclosed embodiments are simply exemplary embodiments of the inventive concepts disclosed herein and should not be considered as limiting, unless the claims expressly state otherwise.

The following examples are intended to illustrate the present invention and to teach one of ordinary skill in the art how to use the formulations of the invention. They are not intended to be limiting in any way.

EXAMPLE

Method

Five, eight-ounce bottle of lidocaine gel containing 3.75% w/v lidocaine hydrochloride, 2.25% w/v HPMC and 0.07% w/v methyl paraben at a pH of 4.5 were loaded with the following bacteria or fungi known to cause serious illnesses in humans: *Pseudomonas aeruginosa* (ATCC No. 9027), *Escherichia coli* (ATTC No. 8739) and *Staphylococcus aureus* (ATCC No. 653 8), *Candida albicans* (ATCC 10231) and *Aspergillus brasiliensis* (ATCC 16404) and incubated at room temperature for 28 days to test for antimicrobial ability of the composition. Results are shown in Table 1 below.

TABLE 1

Antimicrobial Properties of a Lidocaine Gel Composition of the Present Invention

| Microbe | Initial CFU/mL | 14 days CFU/mL | Log Reduction | 28 days CFU/mL | Log Reduction |
|---|---|---|---|---|---|
| P. aeruginosa | $3.0 \times 10^5$ | <10 | 5.5 | <10 | 5.5 |
| E. coli | $5.4 \times 10^5$ | $1.1 \times 10^2$ | 3.7 | <10 | 5.7 |
| S. aureus | $1.4 \times 10^5$ | <10 | 5.1 | <10 | 5.1 |
| C. albicans | $3.0 \times 10^5$ | $8.6 \times 10^3$ | 1.6 | $3.9 \times 10^3$ | 1.9 |
| A. brasiliensis | $1.6 \times 10^5$ | $2.8 \times 10^4$ | 0.8 | $1.1 \times 10^4$ | 1.2 |

As demonstrated in Table 1, the use of methyl paraben as the sole preservative reduced the bacterial load to less than 10 colony forming units per milliliter ("CFU/mL") for each of *P. aeruginosa, E. coli* and *S. aureus*. Further, the use of methyl paraben, alone, reduced fungal load by at least log 1.2 for each of *C. albicans* and *A. brasiliensis*. This data demonstrates that compositions of the present invention containing only 0.07% methyl paraben as a preservative are capable of restricting and reducing the growth of microbes and meets USP-39<51> requirements for Antimicrobial Effectiveness for topically used aqueous based formulations.

What is claimed is:

1. An aqueous gel composition comprising an effective amount of a local anesthetic, a lubricating agent and a preservative, wherein the composition has a pH from about 3.5 to about 4.5 and a viscosity from about 2,000 to about 8,000 centipoise and is topically administered to the vulvovaginal region.

2. The aqueous gel composition of claim 1, wherein the composition is free of polyethylene oxides and sulfated polysaccharides.

3. The composition of claim 1, wherein the local anesthetic is selected from the group consisting of lidocaine, procaine, ropivacaine, bupivacaine, prilocaine and dibucaine and salts thereof.

4. The composition of claim 1, wherein the local anesthetic is lidocaine or salts thereof.

5. The composition of claim 1, wherein the lubricating agent is a cellulose derivative.

6. The composition of claim 5, wherein the cellulose derivative is hydroxypropylmethyl cellulose.

7. The composition of claim 1, wherein the preservative is selected from the group consisting of methyl paraben, propyl paraben, butyl paraben, benzyl paraben, methylcellulose, polyethylene glycol, polyvinylpyrrolidone, polyoxyethylene monostearate, polyoxyethylene sorbitan monolaurate, polyoxyethylene sorbitan monooleate and a combination thereof.

8. The composition of claim 1, wherein the preservative is methyl paraben.

9. The composition of claim 1, wherein the composition is topically administered to the vulvar vestibule.

10. An aqueous gel composition comprising from about 3.5% to about 4.0% w/v of a local anesthetic, from about 2% to about 3% w/v of a lubricating agent and from about 0.07% to about 0.09% w/v of a preservative, wherein the composition has a pH from about 3.5 to about 4.5 and a viscosity from about 2,000 to about 8,000 centipoise and is topically administered to the vulvovaginal region and wherein w/v denotes weight by volume of the composition.

11. The composition of claim 10, wherein the local anesthetic is lidocaine or salts thereof.

12. The composition of claim 10, wherein the lubricating agent is hydroxypropylmethyl cellulose.

13. The composition of claim 10, wherein the preservative is methyl paraben.

14. The composition of claim 1, wherein the composition is topically administered to the vulvar vestibule.

15. An aqueous gel composition comprising about 3.75% w/v lidocaine or salts thereof, about 2.25% w/v hydroxypropylmethyl cellulose and about 0.07% w/v methyl paraben, wherein the composition has a pH of about 4.5 and the viscosity of the composition is of about 6,100 centipoise and is topically administered to the vulva vestibule and wherein w/v denotes weight by volume of the composition.

16. The composition of claim 15, wherein the lidocaine is lidocaine hydrochloride.

17. A method of treating vulvovaginal pain comprising topically administering the composition of claim 1 to a patient in need thereof.

18. The method of claim 16, wherein the vulvovaginal pain is dyspareunia.

19. The method of claim 17, wherein the dyspareunia is associated with genitourinary syndrome of menopause.

20. The method of claim 16, wherein the composition is applied immediately prior to sexual activity.

* * * * *